US00PP09470P

United States Patent [19]

Zaiger et al.

[11] Patent Number: Plant 9,470

[45] Date of Patent: Mar. 12, 1996

[54] PEACH TREE 'SNOW FIRE'

[76] Inventors: Chris F. Zaiger, 929 Grimes Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 406,133

[22] Filed: Mar. 17, 1995

[51] Int. Cl.[6] ..... A01H 5/00

[52] U.S. Cl. ..... Plt./42.1

[58] Field of Search ..... Plt./42.1

*Primary Examiner*—James R. Feyrer

[57] ABSTRACT

A new and distinct variety of peach tree which has the following unique combination of features that are desirable in a new variety:

1. Mild, sweet, subacid fruit with excellent flavor and eating quality.
2. Heavy and regular production of fruit.
3. Fruit with a high degree of attractive red skin color.
4. Large, firm, white flesh, freestone fruit.
5. Fruit with good handling and shipping quality.
6. Vigorous upright growth.

1 Drawing Sheet

ORIGIN OF THE VARIETY

The present new variety of peach tree was developed by us in our experimental orchard located near Modesto, Calif., as a first generation cross between two selected seedlings with the field identification Nos. 108ED290 and 161GD199. The female parent with the field identification No. 108ED290 originated from a cross of a seedling selection indentified as 24GA764 ((Red Grand Nectarine (U.S. Plant Pat. No. 1,060)×Redwing Peach (U.S. Plant Pat. No. 621)) crossed with Sugar Lady Peach (U.S. Plant Pat. No. 7,532). The pollen parent 161GD199 originated from a cross of Ruby Gold Nectarine (U.S. Plant Pat. No. 3,101)×Redwing Peach (U.S. Plant No. 621). We grew and maintained a large group of these first generation seedlings under close observation and one such seedling, which is the present variety, having especially desirable fruit characteristics was selected for asexually propagation and commercialization.

ASEXUAL REPRODUCTION OF THE VARIETY

The new and distinct variety of peach tree was asexually propagated by budding, as performed by us in our experimental orchard, located near Modesto, Calif., which shows that all characteristcs run true to the original tree and are established and transmitted in succeeding propagations.

SUMMARY OF THE VARIETY

The new and distinct variety of peach tree is of large size, vigorous upright growth and is a regular and productive bearer of large, freestone, white flesh fruit with excellent flavor and eating quality. The fruit is further characterized by having firm flesh, having good handling and shipping quality, holding on the tree 6 to 8 days after maturity (shipping ripe), having an attractive red skin color and in comparison to Giant Babcock Peach (U.S. Plant Pat. No. 1,353) the fruit of the new variety has firmer flesh, greater handling and shipping quality and is approximately 3 weeks later in maturity.

DESCRIPTION OF THE PHOTOGRAPHS:

The accompanying color photographic illustration shows typical specimens of the foliage and fruit of the present new variety of peach tree. The upper and lower surface of the leaves are illustrated with an exterior and sectional view of the fruit divided in the suture plane to show flesh coloration, pit cavity and a stone remaining in place. The photographic illustration was taken shortly after being picked at maturity (shipping rip) and the colors are as nearly true as reasonably possible in a color representation of this type.

DESCRIPTION OF THE VARIETY

The following is a detailed botanical description of the present new variety of peach tree, its flowers, foliage and fruit, as based on observations of specimens grown near Modesto, Calif., with terminology (except those in common terms) referenced to Reinhold Color Atlas by A. Kornerup and J. H. Wanscher.

Tree:

*Size.*—Large.
*Vigor.*—Vigorous.
*Growth.*—Upright.
*Density.*—Medium dense.
*Productivity.*—Productive.
*Bearing.*—Regular.

Trunk:

*Size.*—Medium.
*Texture.*—Medium shaggy.
*Color.*—Brown to soot brown (5-E-4) to (5-F-5).

Branches:

*Size.*—Medium.
*Texture.*—Smooth to medium rough. Varies with maturity.
*Lenticels.*—Medium number. Medium size.
*Color.*—Light brown to brown (5-D-5) to 5-E-7). Varies with maturity.

Leaves:

*Size.*—Large. Average length — 7". Average width 1⅝".
*Margin.*—Crenate.
*Form.*—Lanceolate — pointed.
*Thickness.*—Medium.
*Texture.*—Smooth.
*Petiole.*—Medium length. Medium thickness.
*Glands.*—Number varies from 1 to 4. Average number 3. Reniform. Medium size. Located on base of leaf blade and upper portion of petiole.
*Color.*—Upper surface — green to deep green (28-E-8 to 28-F-8). Lower surface — dull green to green (28-E-6 to 28-D-5).

Flower buds:

*Size.*—Medium to large.
*Form.*—Plump.
*Pubescence.*—Pubescent.

Flowers:

*Size.*—Large — showy.

*Blooming period.*—Mar. 5, 1994 to Mar. 10, 1994. Varies slightly with climatic conditions.

*Pollen.*—Present.

*Color.*—Pink.

Fruit:

*Maturity when described.*—Firm ripe.

*Date of first picking.*—Aug. 2, 1994.

*Date of last picking.*—Aug. 8, 1994.

*Size.*—Large. Average diameter axially 3⅛". Average transversely in suture plane 3¼".

*Form.*—Nearly Globose — slightly flattened at stem end.

*Suture.*—Shallow, extends from base to apex.

*Ventral surface.*—Nearly rounded, very slightly lipped.

*Cavity.*—Rounded to slightly enlonged in suture plane. Average depth ½". Average breadth 1".

*Base.*—Retuse.

*Apex.*—Varies from rounded to slight pistil point.

Flesh:

*Ripens.*—Evenly.

*Texture.*—Firm.

*Fibers.*—Few, small, tender.

*Juice.*—Moderate.

*Amygdalin.*—Undetected.

*Flavor.*—Excellent.

*Eating quality.*—Excellent.

*Aroma.*—Moderate.

*Color.*—White to pale white (2-A-1 to 2-A-2). Pit cavity — red to cardinal red (10-C-8 to 10-D-8). Bleeding of red into flesh around pit cavity.

Skin:

*Thickness.*—Medium.

*Texture.*—Medium — tenacious to flesh.

*Tendency to crack.*—None.

*Down.*—Moderate amount. Medium length.

*Color.*—Ground color — white to pinkish white (8-A-1 to 8-A-2). Overspread with red to turkish red (10-C-6 to 10-C-8).

Stone:

*Type.*—Freestone.

*Size.*—Large. Average length 1½". Average width 1⅛". Average thickness ¾".

*Form.*—Obovate.

*Base.*—Usually rounded, varies from straight to rounded.

*Sides.*—Equal to unequal.

*Surface.*—Irregularly furrowed toward apex, pitted toward base. Pit cavities vary from round to elongated.

*Ridges.*—Usually rounded, varies from rounded to narrow.

*Apex.*—Acuminate.

*Tendency to split.*—None.

*Color.*—Brown to chestnut brown (6-E-7 to 6-F-7).

Use:

*Market.*—Local and Long distance.

Keep quality: Good.

Shipping quality: Good.

The new variety of peach tree, its flowers, foliage and fruit, herein described may vary in slight detail due to climate, soil conditions, and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous upright growth and by being a regular and productive bearer of large, firm, white flesh, freestone fruit with excellent flavor and eating quality; the fruit is further characterized by having an attractive red skin color, having good handling and shipping quality and in comparison to Giant Babcock Peach (U.S. Plant Pat. No. 1,353) the fruit has firmer flesh, greater red skin color and is approximately 3 weeks later in maturity.

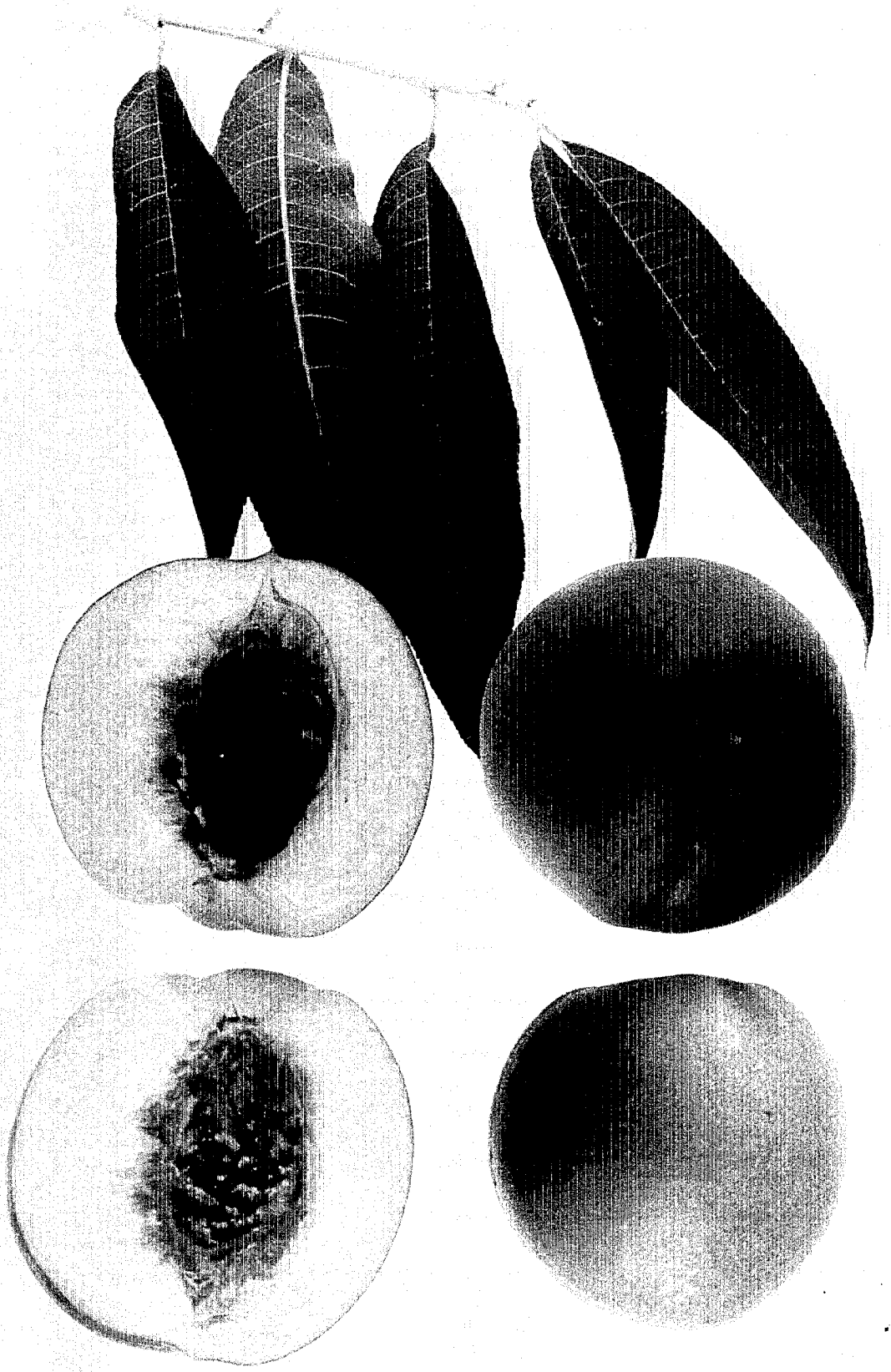

* * * * *